United States Patent [19]

Baggio et al.

[11] Patent Number: 5,686,432
[45] Date of Patent: Nov. 11, 1997

[54] USE OF SOME GLYCOSAMINOGLYCANS IN THE PERITONEAL DIALYSIS

[75] Inventors: Bruno Baggio, San Martino di Lupari; Giorgio Bazzato, Padova; Agostino Fracasso, Mogliano V.; Giovanni Gambaro, Scorze'; Egidio Marchi; Gianfranco Tamagnone, both of Casalecchio di Reno, all of Italy

[73] Assignee: Alfa Wassermann S.p.A., Alanno, Italy

[21] Appl. No.: 530,597

[22] Filed: Sep. 19, 1995

[30] Foreign Application Priority Data

Oct. 6, 1994 [IT] Italy .................. B094A0436

[51] Int. Cl.⁶ .......................... A61K 31/73; A61K 31/725
[52] U.S. Cl. .................................. 514/56; 604/29
[58] Field of Search .................. 514/210, 56, 822; 210/645; 604/29

[56] References Cited

U.S. PATENT DOCUMENTS

| | | | |
|---|---|---|---|
| 5,236,910 | 8/1993 | Egidio et al. | 514/56 |
| 5,496,807 | 3/1996 | Marchi et al. | 514/52 |

OTHER PUBLICATIONS

Naito et al., "Blood Purification Method for High Risk Patient", Kidney and Dialysis, vol. 31, No. 1, pp. 187–190, 1991, ISSN: 0385–2156, Abstract Only.

Breborowicz et al., "Effects of Chondroitin Sulphate on Fluid and Solute Transport During Peritoneal Dialysis in Rats", Peritoneal Dialysis Int., 11(4), pp. 351–354, 1991, Abstract Only.

Breborowicz et al., "Chondroitin Sulphate and Peritoneal Permeability", Advances in Peritoneal Dialysis, vol. 8, pp. 11–14, 1992, Abstract Only.

Breborowicz et al., "The glycosaminoglycan Chondroitin Sulphate Prevents Loss of Ultrafiltration During Peritoneal Dialysis", Nephron, vol. 67, No. 3, pp.346–350, 1994, Abstract Only.

*Primary Examiner*—Joseph L. Schofer
*Assistant Examiner*—Robert H. Harrison
*Attorney, Agent, or Firm*—Bucknam and Archer

[57] ABSTRACT

The use of some glycosaminoglycans like sulodexide, low molecular weight heparin and low molecular weight dermatan sulfate and of the medicines by parenteral use that contain them in the treatment of patients suffering from chronic renal insufficiency subjected to peritoneal dialysis is described. The effectiveness of this use has been shown both by pharmacological studies carried out in nephrectomized rats to whom a peritoneal damage has been caused and by clinical studies carried out in patients suffering from chronic renal insufficiency subjected to CAPD and treated by intraperitoneal route (i.p.) with 2 ml vials of VESSEL DUE F® containing 50 mg of sulodexide. A significant increase of the peritoneal transports of urea and of creatinine joined to a significant decrease of the protein-loss in the peritoneal effluent has been observed. Significant changes of the ultrafiltration capacity and of haemorrhagic-coagulative complications have not been observed during the study.

6 Claims, No Drawings

USE OF SOME GLYCOSAMINOGLYCANS IN THE PERITONEAL DIALYSIS

FIELD OF THE INVENTION

This invention relates to a method for the treatment of patients suffering from chronic renal insufficiency subjected to peritoneal dialysis.

BACKGROUND OF THE INVENTION

The chronic renal insufficiency is a pathology of remarkable clinical and socio-economic importance. The patients suffering from this pathology have to turn to a chronic substitutive treatment of extracorporeal dialysis or of peritoneal dialysis, this latter by Continuous Ambulatory Peritoneal Dialysis (CAPD).

The CAPD technique during the last years has found an always growing use both because of the cheaper costs in comparison with those of the extracorporeal dialysis and for the easiness of execution which does not require the use of sophisticated equipments.

During the first years of its use the CAPD met with a lot of complications, peritonitis has been the most fearful, which limited its use and which during the time can cause peritoneal fibrosis and lowering of the capacity of peritoneal transport, as reported by Fracasso A. and Bazzato G. in "Peritonitis during CAPD" at page 623 of the book "CAPD" edited by Di Paolo N. published in 1991 by Editoriale Bios of Cosenza.

The new techniques of connection and the use of disinfectants have notably lowered the frequency of the peritonitis, as reported by Buoncristiani U. et al., Dial. Transpl. 12, 14, (1983) while at present the problem of the gradual loss during the time of the function and vitality of the peritoneal membrane persists with consequent lowering of the capacity and selectivity of transport of the solutes as reported by Di Paolo N. et al., Nephron, 44, 204, (1986).

This depends on the progressive evolution of structural and functional alterations of the peritoneum that become always more evident with the passing of the dialysis treatment by limiting its therapeutical effectiveness as Di Paolo N. et al. showed at page 11 of the book "Peritoneal dialysis" edited by La Greca and published in 1985 by Wichtig of Milan. Serious proteins losses in patients already weakened from the nutritional point of view can be found because of the worsening of the performance of the peritoneal membrane.

No product at present exists, to our knowledge, that can be used in CAPD so as to prevent the structural and functional alterations of the peritoneal membrane. Such alterations cause the worsening of the peculiar characteristics of vitality, ultrafiltration capacity and selectivity of transport of the membrane essential for granting the therapeutical effectiveness of the dialysis treatment.

The years of treatment with CAPD will be prolonged and the resort to the extracorporeal dialysis will be delayed by solving such problems.

The ability of the sulodexide, a glycosaminoglycan of natural origin made by a heparin fraction having a low anticoagulant activity and by a dermatan fraction, of preventing and curing the nephropathy caused by the diabetes, by fighting against the phenomena that cause the alterations of the renal structure and function has been shown in the European Patent Publication EP 0624374.

Gotloib L. et al., Perit. Dial. Bulletin, 5, 212, (1985) pointed out how the peritoneal membrane shows structural and functional alterations during CAPD very similar to those observed in the proteinuric nephrotic syndromes. The similarity of such pathologic effects is due to the fact that the structural and functional alterations which occur at the level of the peritoneum during the dialysis closely follow the mechanism of the nephrotic syndrome.

On the basis of such remarks some glycosaminoglycans like sulodexide, low molecular weight heparin and low molecular weight dermatan sulfate can be taken into consideration as possible active principles for treating patients suffering from chronic renal insufficiency subjected to peritoneal dialysis.

SUMMARY OF THE INVENTION

An object of the present invention is the therapeutic use of some glicosaminoglycans like sulodexide, glycosaminoglycan of natural origin also known as glucuronylglycosaminoglycan sulfate having a sulfation degree and an anticoagulant activity lower than those of heparin, low molecular weight heparin and low molecular weight dermatan sulfate and of the medicines containing them in the treatment of the patients suffering from chronic renal insufficiency subjected to peritoneal dialysis.

Sulodexide (INN), a glycosaminoglycan of natural origin marketed under the trademark VESSEL DUE F®, parnaparin (INN), low molecular weight heparin having a molecular weight equal to 4500±1000 Daltons obtained by depolymerization of the heparin with cupric acetate, hydrogen peroxide and ascorbic acid and marketed under the trademark FLUXUM® and the low molecular weight dermatan sulfate having molecular weight comprised between 3500 and 8000 Daltons obtained by depolymerization of the dermatan sulfate with cupric acetate and hydrogen peroxide as described in the European Patent EP 0221977 are preferred in the fulfillment of the present invention.

The therapeutically effective dosages for this treatment depend both on the glycosaminoglycan used and on the kind of patient and can vary between a minimum of 20 and a maximum of 500 mg a day. The daily dose preferred in the fulfillment of the present invention is comprised between 40 and 250 mg of glycosaminoglycan a day and can be administered in one or more of the five daily treatments of CAPD usually prescribed in the patients suffering from terminal uremia.

Vials containing the glycosaminoglycans in solution for parenteral use, which are added to the liquid for the dialysis administered by intraperitoneal route, are the pharmaceutical preparations preferred in the fulfillment of the present invention.

Vials containing sulodexide in solution for parenteral use, for instance the medicine marketed under the trademark VESSEL DUE F® whose 2 ml vials have a lipasemic activity equal to 600 S.L.U. and contain 50 mg of sulodexide in sterile physiologic solution, and vials containing low molecular weight heparin known as parnaparin (INN) marketed under the trademark FLUXUM®, whose 0.3 ml vials have an antithrombotic activity equal to 3200 I.U. aXa and contain 40 mg of parnaparin in sterile physiologic solution, are preferably used.

The use of the glycosaminoglycans improves the performance of the CAPD by lowering in particular the protein-loss in the dialytic liquid because it prevents the structural and functional alterations by improving the capability and the selectivity of filtration of the membrane. Their use can, consequently cause a prolongation of the periods of treatment with the CAPD so delaying the need of turning to the extracorporeal dialysis.

The therapeutic effectiveness and the lack of side effects of some glycosaminoglycans in the peritoneal dialysis have been shown by experimental studies in an animal model and by a clinical trial in man.

In the experimental pharmacological studies the rats have been submitted to a treatment with diethylhexylphthalate in order to cause the peritoneal damage according to the method described by Fracasso A. et al., Trans. ASAIO, 33, 3, (1987), after the induction of the renal insufficiency by subtotal nephrectomy.

Subsequently the rats have been divided in two equal groups, to one (treated group) a glycosaminoglycan has been administered for 7 days by subcutaneous route while the other (control group) has not been given any administration of glycosaminoglycan.

Subsequently both groups of rats have been submitted to three cycles of peritoneal dialysis and the values of essential parameters like the ratio between the concentration of the urea in the dialytic liquid and in the plasma (D/P), the protein-loss, the ratio between the final and basal concentration of the glucose in the dialytic liquid (D/Do) and the capability of ultrafiltration that are considered indispensable to show the effectiveness and the selectivity of the transport of peritoneal membrane have been evaluated.

The experimental studies have been carried out on a representative number of rats, as described in detail in the examples reported to illustrate the invention without limiting it. These pharmacological studies have clearly shown the achievement of this object of the present invention because the treatment with all the tested glycosaminoglycans caused a significant improvement of the parameters indicating the effectiveness of the dialysis. In particular, the animals treated with the glycosaminoglycans have shown, in comparison with the controls, a significant lowering of the peritoneal loss of proteins and a significant increase of the excretion of metabolic toxic substances having low molecular weight like urea.

The variations of the values of these parameters are considered as recognized indexes of the improvement of the peritoneal functionality and find a remarkable check in the microscopic surveys that show a lowering of the degenerative processes and of the morphological structural alterations of the peritoneum.

The clinical test, carried out in order to confirm the experimental data obtained in the animal model and to show the therapeutic effectiveness in man of one of the glycosaminoglycans, precisely the sulodexide, envisaged the daily treatment with sulodexide for one month of patients subjected for at least three years to a dialytic treatment by CAPD. After a month of treatment with sulodexide, a period of time of the same length has been scheduled in which the CAPD has been carried out without the contemporaneous administration of the drug, period named in technical jargon "wash out".

Essential parameters like the D/P of the urea, the D/P of the creatinine, the protein-loss and the net ultrafiltration indispensable to show the effectiveness and the selectivity of the dialytic treatment have been compared among them to evaluate the therapeutical effectiveness of the sulodexide. Such values have been checked before the starting, at the end of the treatment with sulodexide and at the end of the period of "wash out".

The clinical test has been carried out on a representative number of patients suffering from chronic renal insufficiency in the manner described in example 4 reported to show the invention without limiting it. A dose of 50 mg of sulodexide contained in a 2 ml vial of the medicine marketed under the trademark VESSEL DUE F® has been administered by intraperitoneal route to the patients submitted, as usual, to five daily exchanges of dialytic solution, together with the liquid of dialysis of the last treatment, i.e. the night-treatment.

The clinical study has clearly shown the achievement of the goal of the present invention because the values of the parameters indicating the effectiveness of the dialytic treatment have significantly been improved at the end of the period of treatment with sulodexide. The improved selectivity of the transport of membrane continued during the time, as shown by the trend of the values of the parameters tested which continued to be better than the basal values also after the suspension of the treatment. In particular, the clinical results showed a significant lowering of the protein-loss and a significant increase of the peritoneal transport of urea and creatinine. The clinical results have fully confirmed the pharmacological results, showing how the treatment with sulodexide is able to lower the peritoneal protein-loss and to increase the elimination of the toxic substances having a low molecular weight. The results of the pharmacological tests in the animal and of the clinical treatment in man have altogether shown how the glycosaminoglycans have significantly improved the selective transport of membrane and have lowered the protein-loss considered of fundamental importance in the renal pathology characterized by serious nutritive deficiencies.

The examples reported hereinbelow have to be considered as a further illustration of the invention and not as an its limitation.

EXAMPLE 1

Treatment with Sulodexide of Nephrectomized Rats

Twenty male Sprague Dawley rats, weighing between 250 and 350 grams, with chronic renal insufficiency induced by subtotal nephrectomy with removal of 5/6 of the renal parenchime (monolateral nephrectomy and upper and lower polectomy of the contralateral kidney) have been used in the study. After 15 days of rest the rats have been treated with a dose of diethylhexylphthalate equal to 0.35 mg/kg of corporeal weight once a day for 7 days so that to cause peritoneal fibrosis according to the method described by Fracasso A. et al., Trans. ASAIO, 33, 3, (1987). Ten of these rats have been used as control group while to the other ten, treated group, 10 mg/kg of body weight of sulodexide have been administered by subcutaneous route for a period of 7 days. Three days after the end of the treatment the rats of both groups, under general anesthesia, have been subjected to 3 cycles of CAPD (12 minutes of standing and 3 minutes for the drainage) with 20 ml of dialytic solution containing 2% of glucose.

The following parameteres have been evaluated on haematic samples and on peritoneal samples of the drainage liquid:

1. ratio between the concentrations of urea in the dialytic liquid and in the plasma (D/P urea);
2. net ultrafiltration (UF);
3. clearance of the albumine (clear. alb.);
4. ratio between the end and basal concentrations of the glucose in the dialytic liquid (D/Do).

Moreover a sample of peritoneal membrane has been taken from each rat for the optical and electronic microscopy.

The data reported in table 1 show how the treatment with sulodexide has caused a significant increase of the transport of urea and of the capability of ultrafiltration together with a significant lowering of the clearance of the albumin and of the D/Do.

TABLE 1

| RATS | D/P urea | UF | Clear. alb. | D/Do |
|---|---|---|---|---|
| Control Group | 0.22 ± 0.03 | 0.46 ± 0.3 | 40.7 ± 9.1 | 0.56 ± 0.05 |
| Treated Group | 0.36 ± 0.04 | 1.4 ± 0.63 | 16.6 ± 7.3 | 0.52 ± 0.02 |

The results obtained show how sulodexide prevents the damage caused by the treatment with the toxic agent (diethylhexylphthalate) on the selectivity of transport of the peritoneal membrane. They find corroboration in the morphological data pointed out by the microscopic check that shows the lessening of the interstitial fibretic processes in the peritoneum of the animals treated with sulodexide.

EXAMPLE 2

Treatment with Parnaparin of Nephrectomized Rats

The test has been carried out in the same way as that described in example 1 by using a parnaparin dosage (10 mg/kg of animal) equal to the dosage used for sulodexide in example 1. The experimental data which show the pharmacological effectiveness of parnaparin are reported in table 2 below.

TABLE 2

| RATS | D/P urea | UF | Clear. alb. | D/Do |
|---|---|---|---|---|
| Control Group | 0.26 ± 0.04 | 0.51 ± 0.30 | 37.2 ± 5.9 | 0.55 ± 0.08 |
| Treated Group | 0.42 ± 0.05 | 1.33 ± 0.34 | 14.9 ± 2.2 | 0.49 ± 0.06 |

EXAMPLE 3

Treatment with Low Molecular Weight Dermatan Sulfate of Nephrectomized Rats

The test has been carried out in the same way as that described in example 1 by using a dosage of low molecular weight dermatan sulfate (20 mg/kg of animal) double in comparison with the dosage used for sulodexide in example 1.

The experimental data which show the pharmacological effectiveness of the low molecular weight dermatan sulfate are reported in table 3 below.

TABLE 3

| RATS | D/P urea | UF | Clear. alb. | D/Do |
|---|---|---|---|---|
| Control Group | 0.19 ± 0.03 | 0.51 ± 0.21 | 44.5 ± 7.4 | 0.48 ± 0.04 |
| Treated group | 0.36 ± 0.05 | 1.24 ± 0.40 | 18.6 ± 4.1 | 0.46 ± 0.07 |

EXAMPLE 4

Treatment with Sulodexide of Patients Submitted to CAPD

Sixteen patients suffering from terminal chronic renal insufficiency treated from 32 to 49 months by continuous ambulatory peritoneal dialysis (CAPD) have been used in the study of clinical experimentation. For a period of 30 days the patients have been submitted, as usual, to 5 daily exchanges of solution for peritoneal dialysis.

A 2 ml vial of VESSEL DUE F® containing 50 mg of sulodexide has been added to the nocturnal exchange during 7–8 hours. At the end of the period of treatment with sulodexide a wash out period of 30 days followed.

The following parameters have been evaluated at the starting and the end of the treatment and after 30 days of wash out:
 1. D/P urea;
 2. DIP creatinine;
 3. protein-loss;
 4. net ultrafiltration (UF).

The values of the above mentioned parameters are reported in table 4 below.

TABLE 4

| TIME | D/P urea | D/P creatinine | UF | Protein-loss (mg/24 h) |
|---|---|---|---|---|
| Basal | 0.86 ± 0.09 | 0.78 ± 0.07 | 0.90 ± 0.8 | 13.07 ± 5.85 |
| End of treatment | 0.92 ± 0.05 | 0.82 ± 0.09 | 1.18 ± 0.6 | 9.80 ± 3.78 |
| End of wash out | 0.86 ± 0.11 | 0.75 ± 0.09 | 0.99 ± 1.0 | 12.38 ± 3.09 |

The examination of the data reported in table 4 shows how the treatment with sulodexide caused a significant increase of the peritoneal transports of urea and creatinine together with a significant lowering of the protein-loss in the peritoneal effluent without any significant change of the capability of ultrafiltration.

The study of the coagulative parameters (fibrinogen, I.N.R., PTT and platelets) did not show any significant change during the study, Moreover during this period no haemorrhagic-coagulative complication and no side effect have been found, things that have shown the absolute safety and reliability of the use of sulodexide in the CAPD.

We claim:

1. A method of reducing the structural and functional degeneration of the peritoneal membrane of patients suffering from chronic renal insufficiency which comprises the intraperitoneal administration of therapeutically effective amounts of glycosaminoglycans selected from the group consisting of sulodexide, low molecular weight heparin and low molecular weight dermatan sulfate during the treatment of peritoneal dialysis whereby an increase of excretion of urea and creatinine and a lowering of loss of proteins are achieved.

2. Method according to claim 1 characterized in that the low molecular weight heparin is parnaparin and the low molecular weight dermatan sulfate has a molecular weight between 3500 and 8000 Daltons and is obtained by depolymerization of the dermatan sulfate with cupric acetate and hydrogen peroxide.

3. Method according to claim 1 characterized in that the therapeutically effective amounts are made by daily doses between 40 and 250 mg.

4. A method of reducing the structural and functional degeneration of the peritoneal membrane of a patient suffering from chronic renal insufficiency, said patient being subjected to peritoneal dealysis, which consists of administering intraperitoneally to said patient an effective amount of a glycosaminoglycan selected from the group consisting of sulodexide, low molecular weight dermatan sulfate whereby an increase of excretion of urea and creatinine and a lowering of loss of proteins are achieved.

5. The method according to claim 4 wherein low molecular weight heparin is parnaparin and the low molecular weight dermatan sulfate has a molecular weight between 3500 and 8000 Daltons and is obtained by depolymerization of the dermatan sulfate with cupric acetate and hydrogen peroxide.

6. The method according to claim 4 wherein the therapeutically effective amount is a daily dose between 40 and 250 mg.

* * * * *